United States Patent [19]

Bina

[11] Patent Number: 5,269,760
[45] Date of Patent: Dec. 14, 1993

[54] NON-REUSABLE HYPODERMIC SYRINGE

[76] Inventor: Dale C. Bina, 27W021 Waltz Dr., Wheaton, Ill. 60187

[21] Appl. No.: 791,319

[22] Filed: Nov. 14, 1991

[51] Int. Cl.$^5$ .............................................. A61M 5/00
[52] U.S. Cl. ..................................... 604/110; 604/218
[58] Field of Search ............... 604/110, 187, 218, 192, 604/263, 220

[56] References Cited

FOREIGN PATENT DOCUMENTS 2197792  6/1988  United Kingdom ................ 604/110

Primary Examiner—John D. Yasko
Attorney, Agent, or Firm—Patula & Associates

[57] ABSTRACT

A non-reusable syringe comprised generally of a syringe needle, a syringe cylinder and a push rod/piston assembly. The medication is loaded into the syringe by withdrawing the push rod/piston assembly from the syringe cylinder until one of the pawl reversing notches engages a reversible pawl, at which point the direction of the rod/piston assembly changes and cannot be redirected, whereupon the user is committed. Air then is evacuated from the syringe prior to the injection, which starts the forward injection sequence. Also at this point the retaining ring holding the auto release piston is left behind near the top of the syringe. The injection proceeds to completion normally, with the top of the locking dust cap flush with the top of the syringe. After the injection is completed, the syringe is locked in the farthest down position.

32 Claims, 4 Drawing Sheets

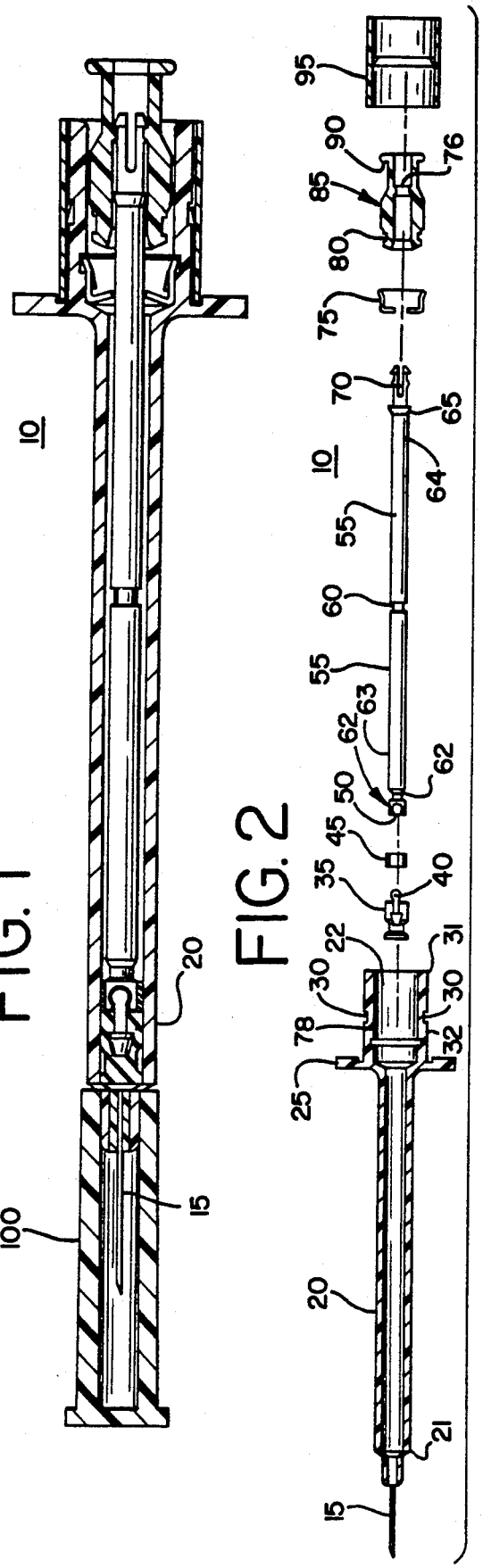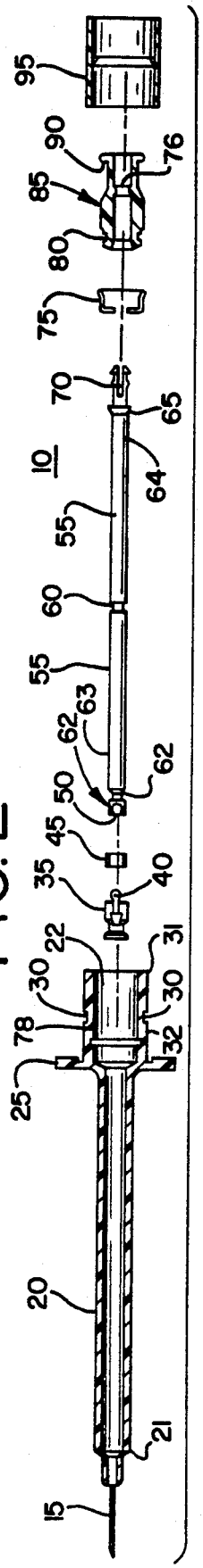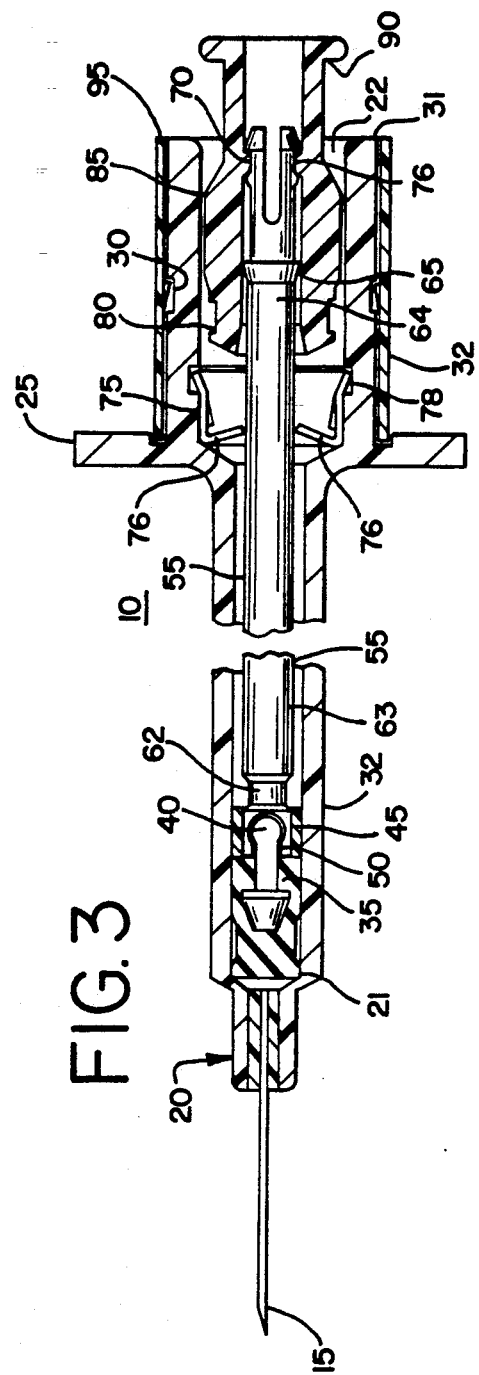

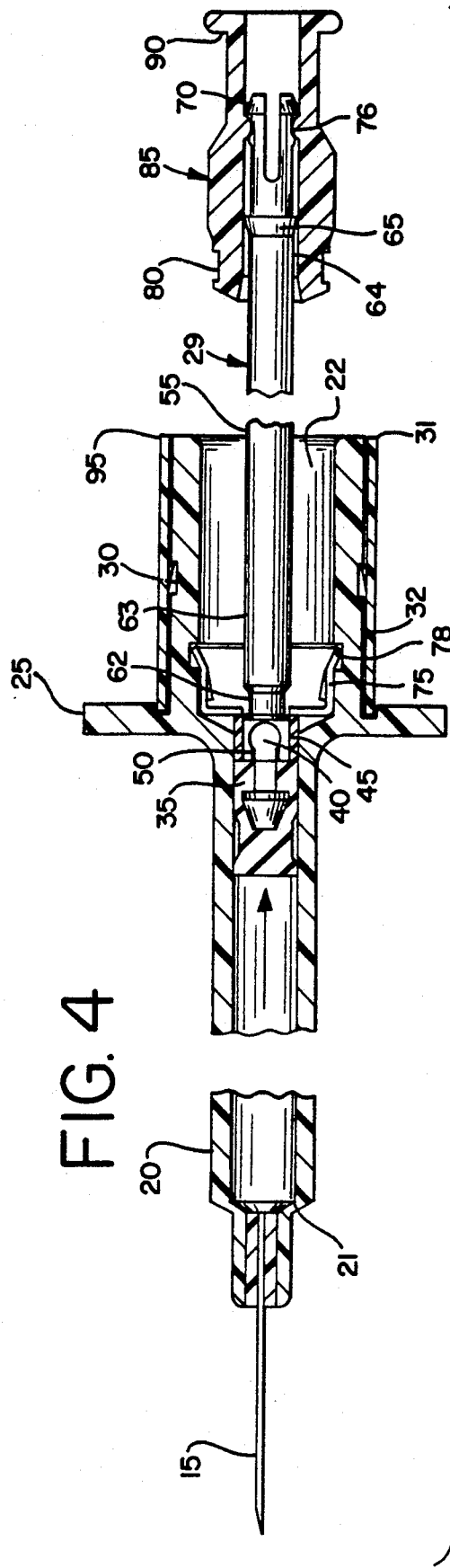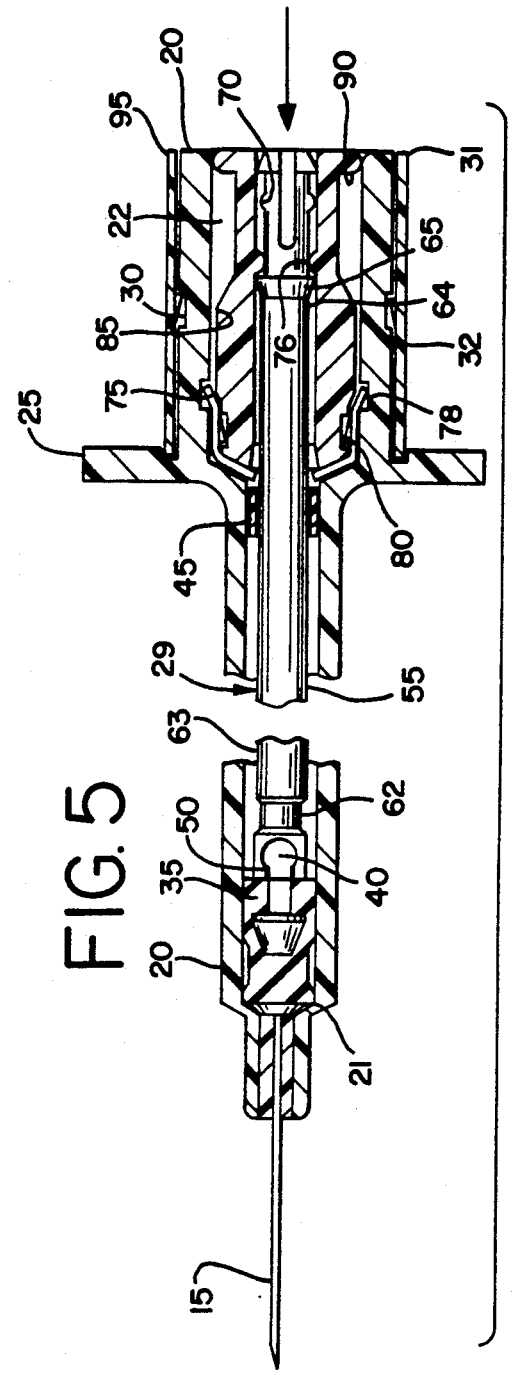

NON-REUSABLE HYPODERMIC SYRINGE

This invention relates to a single use or non-reusable hypodermic syringe used in the intravenous injection of medication and drugs to humans, animals and in other hypodermic applications.

BACKGROUND OF THE INVENTION

The purpose of the present invention is to produce a non-reversible disposable syringe which retains the basic physical and operational characteristics of existing disposable syringes, yet after use is unable to be reused. It is also important that the device be capable of being mass produced economically using existing tooling and manufacturing techniques.

The syringe of the present invention is the same size as existing syringes and can be made as economically as existing syringes, and is tamper resistant. When used with associated features such as a disposal sleeve, the present invention provides a completely new medication delivery system which is safe and sterile from beginning to end.

Over the years, several attempts have been made to design and produce a syringe of this type. These attempts have, to date, been unsuccessful primarily because they did not achieve either the operational goal or the commercial goal. The annual production of disposable syringes numbers in the billions. For example, there are approximately 20 million diabetics in the United States. On the average each diabetic needs two syringes per day, which constitutes a need for over 16 billion syringes for diabetics in the United States alone. This figure does not include uses other than for diabetics, so the need for safe, effective syringes is extremely large. Generally, non-reusable syringes were restricted to pre-loaded syringes, or units with unusual or complicated operations. However, no significant medical or commercial success has been achieved to date by non-reusable syringes currently available.

The underlying goal of the present syringe is the prevention of user self-infection or the spreading of infection by the sharing of syringes, such as is caused by intravenous drug users and abusers.

A number of devices in the past taught a variety of mechanisms to destroy the syringe after use. For example, U.S. Pat. No. 3,951,146 to Chiquiar-Arias positions a blade inside the syringe in such a way as to slice through the syringe during the injection sequence. This device would be cost prohibitive to manufacture and sell due to the structure needed to make the syringe non-reusable. U.S. Pat. No. 3,998,224 to Chiquiar-Arias causes the syringe to be punctured at the end of the injection sequence. Further, there is a small embossed stop at the bottom which captures the push rod at the bottom of the cylinder. It also proposes to plug the needle at the end of the sequence. There is no comparison in operation or structure to the present invention.

U.S. Pat. No. 4,233,975 to Yerman proposes a mechanism which irreversibly clogs itself upon use, but the injection sequence must go to completion to be effective. It also proposes a spring loaded latch which pops into a notch at the bottom of the syringe. It also invokes other locking mechanism which prevent the re-use of the syringe. However, all these mechanisms require special loading and/or for the injection to go to completion, unlike the present invention.

A number of devices utilize pre-filed syringes. For example, U.S. Pat. No. 4,367,738 to Legendre et al. is a one-way pre-filled syringe and has no commonality operationally or mechanically with the present invention. Furthermore, the Legendre et al. device would be difficult to manufacture in comparison to the present invention. U.S. Pat. No. 4,493,703 to Butterfield proposes a syringe using a pre-loaded drop-in cartridge injected via a one way drive piston. This device has no commonality in operation or mechanics with the present invention. U.S. Pat. No. 4,713,056 to Butterfield also proposes a unit that must be pre-loaded. The injection operates via a one-way piston with a latching device which depends on grooves in the barrel of the syringe to guide and capture the piston. This device further uses a pawl mechanism unlike the present invention.

U.S. Pat. No. 4,775,363 to Sandsdalen discloses a self-releasing piston having a different functional implementation. Sandsdalen depends on certain forces being present to deform various of its components to effect the piston's release. The present invention's operation does not depend on injection forces and will operate consistently.

U.S. Pat. No. 4,775,364 to Alles discloses the use of molded-in guides and catches, suction cups, with a break-away push rod to accomplish its goal of non-reusability.

U.S. Pat. No. 4,781,684 to Trenner employs a number of notches in the wall of the barrel to catch flanges on the piston to disable the syringe after use. This is also dissimilar to the present invention.

U.S. Pat. No. 4,820,272 to Palmer utilizes a series of catches, and the unit must be fully injected to lock up the syringe. The device provides tactile feedback to warn the user of impending lock-up. This is done to prevent lock up during the filling operation. This feature almost entirely defeats the purpose of the non-reusability.

A number of devices utilize complicated and expensive structure. U.S. Pat. No. 4,826,483 to Molnar, IV disclosed a complicated arrangement of dual sets of ratchets. U.S. Pat. No. 4,840,616 to Banks uses a series of teeth and splines activated by requiring the user to rotate the plunger. Both are highly dissimilar in operation and structure to the present invention.

BRIEF SUMMARY OF THE INVENTION

The syringe of the present invention is designed to be non-reusable, non-reloadable, and tamper proof. It is comprised generally of a syringe needle, a syringe cylinder and a push rod/piston assembly. In the present invention, the syringe needle is inserted into the medicine receptacle such as a vial. The medication is loaded into the syringe by withdrawing the push rod/piston assembly from the syringe cylinder until one of the pawl reversing notches engages a reversible pawl, at which point the direction of the rod/piston assembly changes and cannot be redirected, whereupon the user is committed. Air then is evacuated from the syringe prior to the injection, which starts the forward injection sequence. Also at this point the retaining ring holding the auto release piston is left behind near the top of the syringe. The injection proceeds to completion normally, with the top of the locking dust cap flush with the top of the syringe. After the injection is completed, the syringe is locked in the farthest down position.

The ability to tamper with the syringe at the point of injection completion is very difficult. The dust cap, which is locked into the pawl, must be pulled out of the neck of the syringe. If this can be done, the push rod is locked in place by the pawl. To remove the pawl, the neck of the syringe, which is protected by a metal sleeve, must be broken. If this is accomplished, the push rod can be pulled out, but the piston is left in the bottom of the syringe with no way to capture it. The syringe is rendered totally useless and thereby achieving the desired goals and objects of the invention.

Alternative embodiments may have other features such as eliminating the reversible pawl or replacing it with a plastic cup or disc which would prevent tampering with the retaining ring. In its simplest form, the syringe would utilize only the auto-release piston.

Further, this used syringe could be disposed of in a disposal tube, which becomes permanently attached to the body of the syringe, preventing accidental needle stick injury or infection. Attempting to remove this disposal tube will cause the syringe to break away, leaving the needle inside the disposal tube.

Numerous other advantages and features of the invention will become readily apparent from the detailed description of the preferred embodiment of the invention, from the claims, and from the accompanying drawings, in which like numerals are employed to designate like parts throughout the same.

BRIEF DESCRIPTION OF THE DRAWINGS

A fuller understanding of the foregoing may be had by reference to the accompanying drawings, wherein:

FIG. 1 is a longitudinal cross-sectional view of the single-use syringe needle of the present invention in its storage or rest state;

FIG. 2 is an exploded longitudinal cross-sectional view of the syringe needle of the present invention;

FIG. 3 is a partial longitudinal cross-sectional view of the present invention showing the needle end and the plunger end of the syringe;

FIG. 4 is a partial longitudinal cross-sectional view of the present invention showing the needle end, midsection and plunger end of the syringe;

FIG. 5 is a partial longitudinal cross-sectional view of the present invention showing the rod/piston actuation at the plunger end of the syringe;

DESCRIPTION OF THE PREFERRED EMBODIMENT

Figure 6:
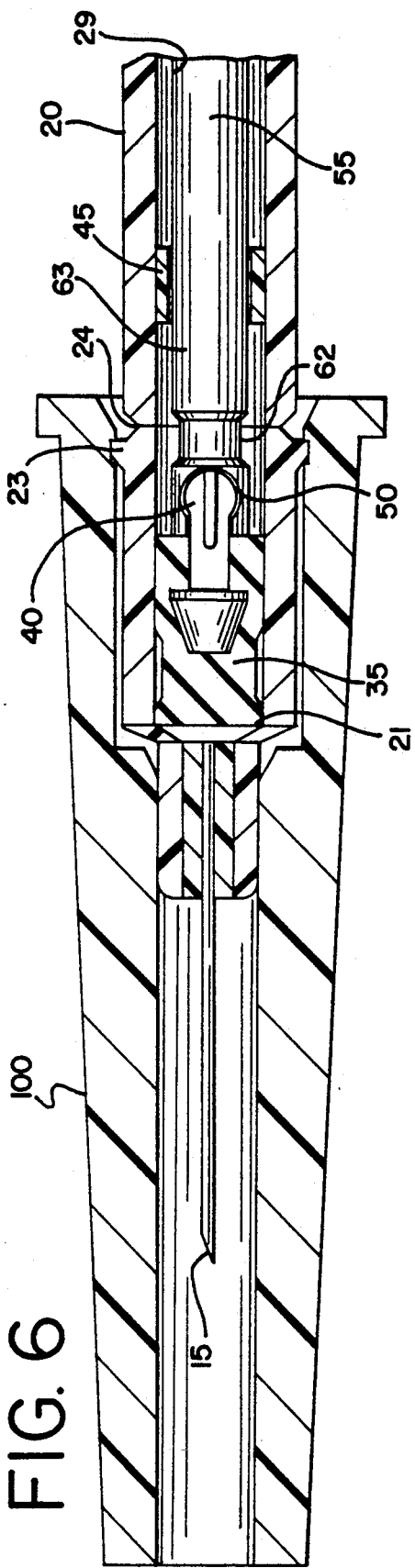
FIG. 6 is a partial longitudinal cross-sectional view of an alternative embodiment of the present invention showing the disposal sleeve locked over the needle of the syringe.

While the invention is susceptible of embodiment in many different forms, it should be understood that the present disclosure is to be considered an exemplification of the principles of the invention and is not intended to limit the spirit and scope of the invention and/or claims of the embodiments illustrated.

As shown in FIG. 1, the device 10 is in its storage or rest state. In this state, a disposal sleeve 100 is positioned over the needle 15 which is affixed to the syringe body 20 for fluid communication therewith.

As shown in FIG. 2, the syringe body 20 is preferably made of plastic but conceivably of rubber or metal and has a needle end 21, a medicine cavity 26, an inner surface of the medicine cavity 27, an actuation end 31 and an outer housing 32. A flange 25, is formed at the actuation end 31 of syringe body 20, said flange 25 having a sleeve retainer notch 30 formed on the outer housing 32. Syringe body 20 has a locking cavity 22 formed at actuation end 31.

Plunger assembly 29 consists of push rod 55 made of plastic but conceivably rubber or metal, and has at plunger end 63 a plunger end engaging notch 62, and an insert capture 50. Piston 35 connects to insert capture 50 via plunger insert 40. A retainer ring 45 made of plastic, metal or rubber is affixed to the piston 35 over plunger insert 40. The retainer ring 45 prevents capture 50 from deforming when the plunger assembly 29 is retracted, in turn preventing the plunger insert 40 from disengaging from the capture 50.

On push rod 55 are pawl reversing notches 60 and 62, as well as a dust cap stop 65 and dust cap stop ring 70. Reversible pawl 75 could be made of plastic metal or rubber and is configured to be fitted coaxially over the push rod 55. The reversible pawl 75 is complementarily configured to be fitted with pawl capture 80 of locking dust cap 85 made of plastic, rubber or metal. Locking dust cap 85 is moved by the use of a dust cap push 90, with anti-tamper sleeve 95 positioned thereover.

Shown in FIGS. 3, 4 and 5 are the typical applications of the preferred embodiment of the present invention. FIG. 3 shows the invention ready to load medication. FIG. 4 illustrates the configuration of the invention after it is completely loaded with medicine, and FIG. 5 shows the configuration of the invention after the medicine is completely evacuated.

In FIG. 3, the device 10 is shown after the disposal sleeve 100 is removed and before the loading of the intravenous medication into the device 10. Note that within the syringe body 20, the piston 35, with plunger insert 40 positioned therein, is bottomed out at 21 within the medicine cavity 26. Note also that pawl capture 80 of locking dust cover 85 is not engaged with reversible pawl 75.

The device is operated first by inserting the needle 15 in a conventional medicine vial containing the medication stored therein. Next, the plunger assembly 29 is pulled out of the syringe body 20, moving the piston 35 from the needle end of the syringe body at 21 in the direction toward the flange 25. Because of the complimentary fit of the piston 35 and the inside surface 27 of the syringe body 20, the backward movement of the plunger assembly 29 creates a vacuum in the medicine cavity 26, drawing the medicine into the medicine cavity 26. As withdrawal continues, the reversible pawl 75 engages the first pawl reversing notch 60, the medicine cavity 26 at that time filled to one half capacity, then continues further until the medicine cavity 26 is completely loaded with medication, and the final pawl reversing notch 62 is engaged.

FIG. 4 shows the invention 10 at the point where the medicine cavity 26 is completely loaded with medicine. At this point of loading, the retainer ring 45 has reached the final resting place, and the plunger end engaging notch 62 has engaged the reversible pawl 75.

The device 10 then is evacuated in normal fashion as you would any other syringe by effecting the ejection sequence through actuation of piston 35. By pushing on dust cap push 90, which is attached to push rod 55, to piston 35 and plunger insert 40, injection proceeds normally until piston 35 is fully seated against the needle end of syringe body 20. Additional force pushes the dust cap stop ridge 76 of locking dust cover 85 past dust cap stop ring 70, so that dust cap 85 is fully seated within the locking cavity 22 of the syringe body 20 as shown in FIG. 5. At this point, the retaining ring 45 remains at the actuation end 31 of the syringe body 20 and will not secure the plunger insert 40 assembly to the push rod 55.

Several features of the preferred embodiment ensure that the syringe will not be reusable. As seen in FIG. 5, if someone were to attempt to reuse the syringe, they would be unable to grasp the dust cap push 90 because it is flush with the surface of the actuation end 31 of the syringe body 20. Moreover, the locking dust cap 85, even if it could be grasped, could not be extracted from the syringe body 20 because the locking dust cap 85 is captured by the reversible pawl 75 at pawn capture 80, and the reversible pawl 75 is in turn captured by the pawl retaining notch 78 in the cavity 22. Thus, once the medicine is dispensed, the entire assembly locks completely shut, making retraction of the plunging assembly 29 impossible.

Further, the push rod 55 is securely captured by the force exerted on it by the reversible pawl 75. As shown in FIG. 3, reversible pawl 75 is positioned such that the push rod 55 mechanism can be withdrawn. Push rod 55 is only able to move in the loading position in one direction because of the angular engagement of the reversible pawl 75 against the push rod 55. When the piston 35 is brought to the top of the syringe body as shown in FIG. 4, plunger end engaging notch 62 allows the reversible pawl 75 to change the angular engagement as the plunger is forced back toward the needle end 21 of the syringe body 20. When the device is completely emptied as shown in FIG. 5, the angular engagement of the reversible pawl 75 remains reversed, and the reversible pawl 75 exerts force against push rod 55 in such a manner as to frustrate any attempt to withdraw the plunger, push rod, and locking dust cap assembly.

Additionally, FIG. 5 shows the retaining ring 45 left near the top of the device 10. Because the retaining ring 45 no longer secures insert capture 50, retracting the push rod 55 would allow insert capture 50 to slip off of plunger insert 40. Since the push rod 55 and piston 35 are disengaged, the piston 35 cannot be moved, thwarting any attempts to draw a liquid into the syringe, and making the device completely useless.

Figure 7:
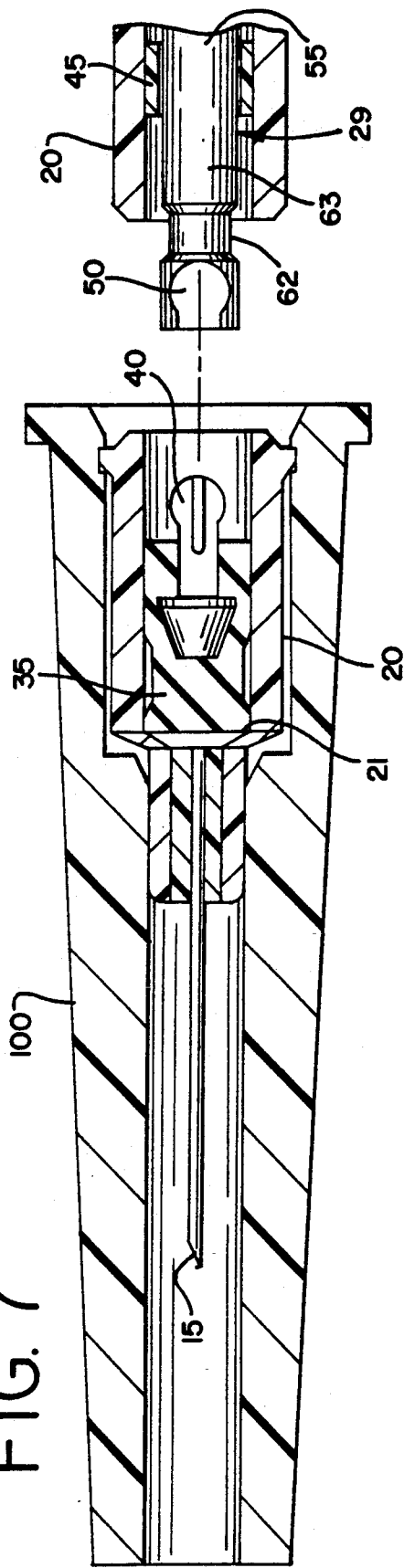
FIG. 7 is a partial longitudinal cross-sectional view of an alternative embodiment of the present invention depicted in FIG. 6, showing the disposal sleeve separated from the syringe body.

In order to prevent skin punctures by a used, dirty needle, FIG. 6 shows in an alternative embodiment that the reversible locking disposal sleeve 100 can be removed from the device 10 after use, reversed and placed over the syringe body 20 such that it catches on disposal sleeve retaining ring 23 and fracture notch 24, which prevents accidental punctures of a dirty needle because of the covering of the reversible locking disposal sleeve 100. Furthermore, if the device was tampered with, the fracture notch 24 would cause the device 10 to break off at the point of the fracture notch 24, as shown in FIG. 7, actually thereby causing a totally inoperative device and capturing the needle 15 within the disposable sleeve 100.

Figure 8:
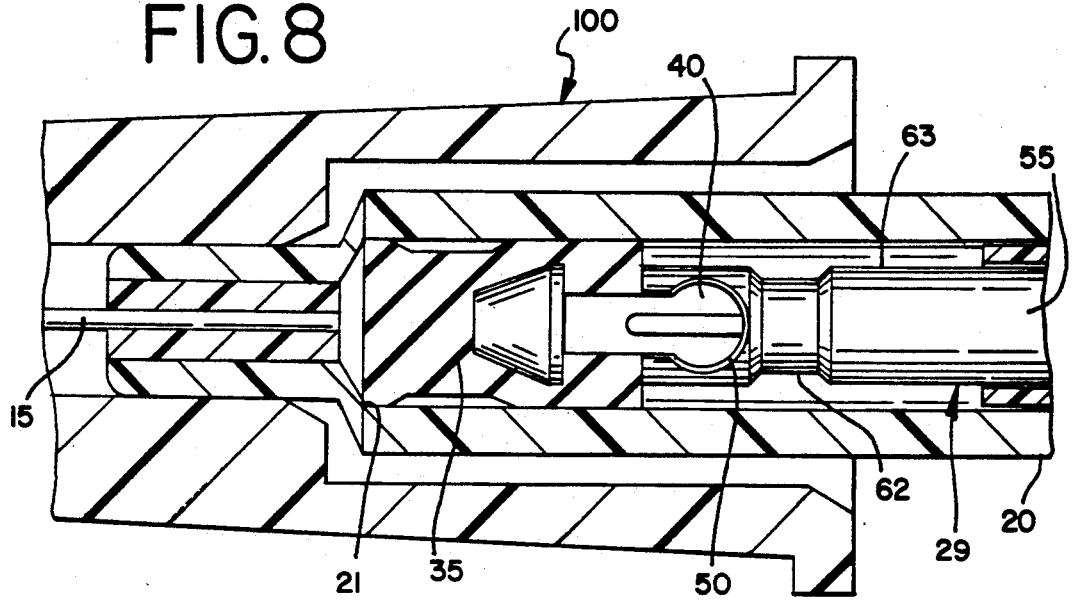
FIG. 8 is an enlarged partial cross-sectional view of the plunger end of the present invention.

FIG. 8 shows the reversible locking disposal sleeve 100 in place, but with no fracture notch 24 or sleeve retaining ring 23 as shown in FIG. 6. According to FIG. 8, if the device 10 was tampered with, such as by pulling push rod 55 out of syringe body 20, the insert 40 would separate from insert capture 50, and the device 10 would again be made inoperative.

Figure 9:
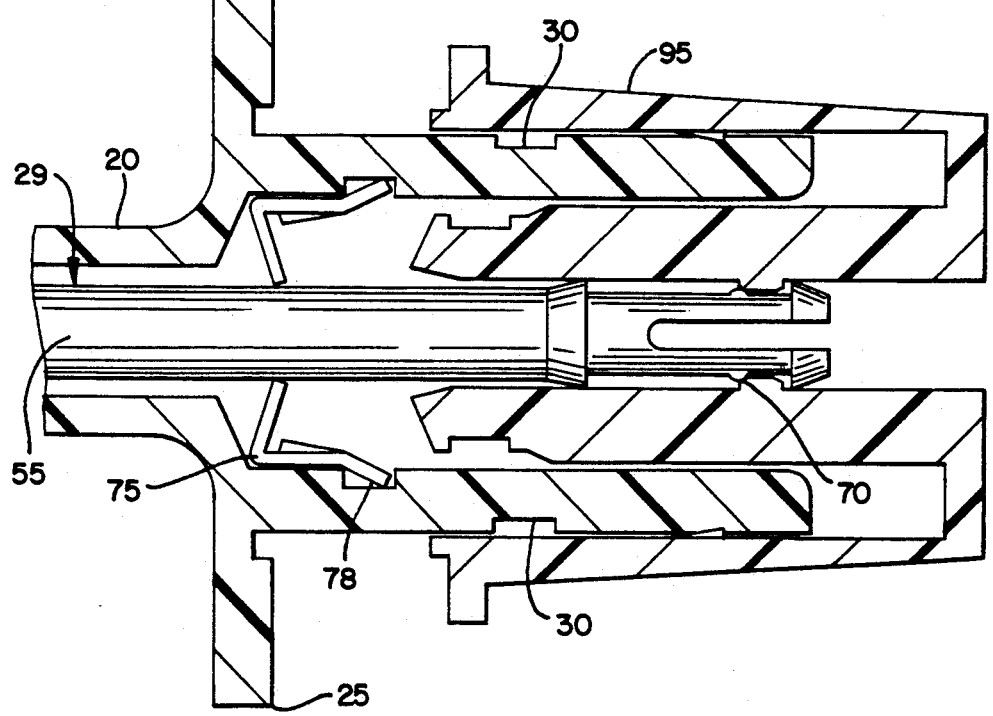
FIG. 9 is an enlarged partial cross-sectional view of the plunger end of the syringe of the present invention.

FIG. 9 is another alternative embodiment in which the anti-tamper sleeve 95 is included with the locking dust cap 85. This embodiment of the invention performs substantially in the same manner as the embodiment depicted in FIGS. 1-5, but differs in that it reduces two components into a single piece.

The foregoing specification describes only the preferred embodiment of the invention as shown. Other embodiments besides may be articulated as well. The terms and expressions therefore serve only to describe the invention by example only and not to limit the invention. It is expected that others will perceive differences which while differing from the foregoing, do not depart from the spirit and scope of the invention herein described and claimed.

What I claim is:

1. A non-reusable hypodermic syringe possible filled with fluid and having a hypodermic needle in fluid communication therewith, comprising:
   a syringe body having an inner surface, and said syringe body having first and second ends, with a locking cavity disposed on said second end;
   a reversible locking pawl disposed in said locking cavity; and
   means for plunging, having first and second ends, said first end having a piston sized to coaxially conform to said inner surface of said syringe body and proximately located at said second end of said syringe body, and said second end sized to lockably engage said locking cavity of said syringe body when said piston is pushed via said plunging means from said second to said first end of said syringe body.

2. The invention of claim 1, wherein said plunging means has a push rod having first and second ends, with said first end being detachably connected to said piston and said second end being connected to a locking dust cap sized to fit said locking cavity of said syringe body, wherein said locking dust cap has a first end and a second end, said first end having a pawl capture sized to engage a reversible pawl, and said second end has a dust cap push and a reversible pawl ridge.

3. The invention of claim 2, wherein said reversible pawl is adapted to fit within said locking cavity and adapted to fit coaxially with said push rod.

4. The invention of claim 3, wherein disposed on said second end of said push rod is a dust cap stop and a dust cap stop ring, both sized to fit within said locking dust cap, said dust cap stop ring disposed to engage said dust cap stop ridge.

5. The invention of claim 4, wherein said syringe body has disposed on its first end a sleeve retaining ring and a means for fracturing said body.

6. The invention of claim 5, having a disposable sleeve adapted to removably fit over the first end of said syringe body, wherein said disposable sleeve has a first end and a second end, said first end removably disposed on said syringe body, said second end adapted to lockingly engage said sleeve retaining ring.

7. The invention of claim 2, wherein said plunger means has a plunger insert, and said first end of said push rod has an insert capture, and disposed on said insert capture is a retaining ring sized to slidably fit over said insert capture and said push rod, said retaining ring further sized to fit within said syringe body.

8. The invention of claim 7, wherein a reversible pawl is adapted to fit within said locking cavity and adapted to fit coaxially with said push rod.

9. The invention of claim 8, wherein said locking dust cap has a first end and a second end, said first end having a pawl capture sized to engage said reversible pawl, and said second end having a dust cap push and a reversible pawl ridge.

10. The invention of claim 9, wherein disposed on said second end of said push rod is a dust cap stop and a dust cap stop ring, both sized to fit within said locking dust cap, said dust cap stop ring disposed to engage said dust cap stop ridge.

11. The invention of claim 10, wherein said syringe body has disposed on its first end a sleeve retaining ring.

12. The invention of claim 11, having a disposable sleeve adapted to removably fit over said syringe body, wherein said disposable sleeve has a first end and a second end, said first end removably disposed on said syringe body, said second end adapted to lockingly engage said sleeve retaining ring.

13. The invention of claim 12, wherein disposed on said syringe body is a means for fracturing said syringe body.

14. A non-reusable hypodermic syringe possibly filled with fluid and having a hypodermic needle in fluid communication therewith, comprising:
   syringe body having a medicine cavity, and a first end and a second end, with a locking cavity disposed on said second end; and
   means for plunging, consisting of a push rod, having a first end and a second end, with said first end being detachably connected to a piston sized to fit said medicine cavity, and said second end being connected to a locking dust cap sized to fit and lockingly engage said locking cavity of said syringe body.

15. The invention of claim 14, wherein a reversible pawl is adapted to fit within said locking cavity and adapted to fit coaxially with said push rod.

16. The invention of claim 15, wherein said locking dust cap has a first end and a second end, said first end having a pawl capture sized to engage said reversible pawl, and said second end having a dust cap push and a reversible pawl ridge.

17. The invention of claim 16, wherein disposed on said second end of said push rod is a dust cap stop and a dust cap stop ring, both sized to fit within said locking dust cap, said dust cap stop ring disposed to engage said dust cap stop ridge.

18. The invention of claim 17, wherein said syringe body has disposed on its first end a sleeve retaining ring and a means for fracturing said syringe body.

19. The invention of claim 18, having a disposable sleeve adapted to removably fit over said syringe body, wherein said disposable sleeve has a first end and a second end, said first end removably disposed on said syringe body, said second end adapted to lockingly engage said sleeve retaining ring.

20. The invention of claim 19, wherein said piston has a plunger insert, and said first end of said push rod has an insert capture.

21. The invention of claim 20, wherein disposed on said insert capture is a retaining ring sized to slidably fit over said insert capture and said push rod, said retaining ring further sized to fit within said medicine cavity.

22. The invention of claim 21, wherein a reversible pawl is adapted to fit within said locking cavity and adapted to fit coaxially with said push rod.

23. The invention of claim 22, wherein said locking dust cap has a first end and a second end, said first end having a pawl capture sized to engage said reversible pawl, and said second end has a dust cap push and a reversible pawl ridge.

24. The invention of claim 23, wherein disposed on said second end of said push rod is a dust cap stop and a dust cap stop ring, both sized to fit within said locking dust cap, said dust cap stop ring disposed to engage said dust cap stop ridge.

25. The invention of claim 24, wherein said syringe body has disposed on its first end a sleeve retaining ring.

26. The invention of claim 25, having a disposable sleeve adapted to removably fit over said syringe body, wherein said disposable sleeve has a first end and a second end, said first end removably disposed on said syringe body, said second end adapted to lockingly engage said sleeve retaining ring.

27. The invention of claim 26, wherein disposed on said syringe body is a means for fracturing said syringe body.

28. A non-reusable hypodermic syringe possibly filled with fluid and having a hypodermic needle in fluid communication therewith, comprising:
   syringe body having a medicine cavity, and a first end and a second end, and on said second end, a locking cavity, a pawl retaining notch disposed within said locking cavity, a flange, an outer housing and a sleeve retaining notch;
   means for plunging having a push rod having a first end and a second end, said first end having an insert capture and a plunger end engaging notch, said second end having a dust cap stop, and a dust cap stopping ring, said push rod further having disposed between said first end and said second end a pawl reversing notch;
   piston, sized to fit within said medicine cavity of said syringe body, and having a plunger insert means adapted to fit within said insert capture of said push rod;
   retainer ring, sized to slidingly fit within said cavity of said syringe body, and adapted to slidingly fit over both said push rod and insert capture;
   reversible pawl adapted to fit within said locking cavity of said syringe body, further adapted to fit within said pawl retaining notch;
   locking dust cap, having a first end and a second end, said first end having a pawl capture adapted to fit within said reversible pawl, and said second end having a dust cap push, said second end further having a dust cap stop ridge adapted to engage said dust cap stop ring of said push rod; and
   disposable sleeve adapted to removably fit over said syringe body.

29. Said invention of claim 28, wherein said syringe body has disposed on its first end a sleeve retaining ring.

30. The invention of claim 29, wherein said disposable sleeve has a first end and a second end, said first end removably disposed on said syringe body, said second end adapted to lockingly engage said sleeve retaining ring.

31. The invention of claim 30, wherein disposed on said syringe body is a means for fracturing said syringe body.

32. The invention of claim 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31, Wherein said locking dust cap forms an anti-tamper sleeve.

* * * * *